United States Patent
Amador Carrascal et al.

(10) Patent No.: US 10,357,226 B2
(45) Date of Patent: Jul. 23, 2019

(54) SYSTEM AND METHOD FOR MODEL-INDEPENDENT QUANTIFICATION OF TISSUE VISCOELASTIC PROPERTIES USING ULTRASOUND

(71) Applicants: Carolina Amador Carrascal, Rochester, MN (US); Matthew W. Urban, Rochester, MN (US); Shigao Chen, Rochester, MN (US); James F. Greenleaf, Rochester, MN (US)

(72) Inventors: Carolina Amador Carrascal, Rochester, MN (US); Matthew W. Urban, Rochester, MN (US); Shigao Chen, Rochester, MN (US); James F. Greenleaf, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1002 days.

(21) Appl. No.: 13/795,199

(22) Filed: Mar. 12, 2013

(65) Prior Publication Data
US 2013/0237821 A1    Sep. 12, 2013

Related U.S. Application Data

(60) Provisional application No. 61/609,645, filed on Mar. 12, 2012.

(51) Int. Cl.
*A61B 8/00*    (2006.01)
*A61B 8/08*    (2006.01)
*G01S 7/52*    (2006.01)

(52) U.S. Cl.
CPC .............. *A61B 8/485* (2013.01); *A61B 8/085* (2013.01); *A61B 8/5223* (2013.01); *G01S 7/52042* (2013.01)

(58) Field of Classification Search
CPC ...................................................... A61B 8/485
USPC ......................................................... 600/438
See application file for complete search history.

(56) References Cited

U.S. PATENT DOCUMENTS

| 4,170,141 A * | 10/1979 | Woo ................................ 73/579 |
| 7,753,847 B2 | 7/2010 | Greenleaf et al. |
| 7,785,259 B2 | 8/2010 | Zheng et al. |
| 2010/0138163 A1 | 6/2010 | Gallippi et al. |

OTHER PUBLICATIONS

Evans, et al., Direct Conversion of Rheological Compliance Measurements Into Storage and Loss Moduli, Physical Review E, 2009, 80(1):012501, 4 pages.

Mauldin, Jr., et al., Monitored Steady-State Excitation and Recovery (MSSER) Radiation Force Imaging Using Viscoelastic Models, IEEE Transactions on Ultrasonics, Ferroelectrics, and Frequency Control, 2008, 55(7)1597-1610.

* cited by examiner

*Primary Examiner* — Rajeev P Siripurapu
(74) *Attorney, Agent, or Firm* — Quarles & Brady LLP (57) ABSTRACT

A model-independent method for producing a viscoelastic tissue property metric using ultrasound is provided. A mechanical stress, such as an acoustic force, is applied to a tissue using an ultrasound system and tissue displacement resulting from the applied acoustic force is measured. From the tissue displacement measurements, a complex modulus, such as a relative complex modulus, is extracted. A loss tangent is calculated from the extracted complex modulus. Using the calculated loss tangent, viscoelastic tissue property metrics may be calculated.

12 Claims, 5 Drawing Sheets

SYSTEM AND METHOD FOR MODEL-INDEPENDENT QUANTIFICATION OF TISSUE VISCOELASTIC PROPERTIES USING ULTRASOUND

CROSS-REFERENCE TO RELATED APPLICATIONS

This application claims the benefit of U.S. Provisional Patent Application Ser. No. 61/609,645, filed on Mar. 12, 2012, and entitled "System and Method for Model-Independent Quantification of Tissue Viscoelastic Properties Using Ultrasound."

STATEMENT REGARDING FEDERALLY SPONSORED RESEARCH

This invention was made with government support under EB002640, EB002167, and DK082408 awarded by the National Institutes of Health. The government has certain rights in the invention.

BACKGROUND OF THE INVENTION

The field of the invention is systems and methods for medical imaging using vibratory energy, such as ultrasound imaging. More particularly, the field of the invention is systems and methods for shear wave dispersion ultrasound vibrometry ("SDUV").

Tissue mechanical properties are linked to tissue pathology state. Shear wave propagation methods have been proposed to quantify tissue mechanical properties. In these methods, shear waves that result from a transient (impulsive or short tone burst) excitation of tissue propagate only a few millimeters, as a result of tissue absorption and shear wave attenuation, therefore boundary condition problems are overcome, allowing us to assume that the shear waves propagate as if in an infinite medium. Shear waves are usually generated by external mechanical vibration or by acoustic radiation force from a focused ultrasound beam. The advantage of using acoustic radiation force is that if an acoustic window is available then the ultrasound system can create a focused beam to apply radiation force to push tissue.

Characterization of tissue mechanical properties, particularly the elasticity or tactile hardness of tissue, has important medical applications because these properties are closely linked to tissue pathology state. Recently, shear wave propagation methods have been proposed to quantify tissue mechanical properties. In general, these methods generate shear waves in tissue by transiently exciting the tissue. These shear wave propagate a short distance, such as only a few millimeters, because of tissue absorption and shear wave attenuation. Shear waves are usually generated by external mechanical vibration or by acoustic radiation force from a focused ultrasound beam. The advantage of using acoustic radiation force is the fact that a pushing pulse of radiation force can be applied anywhere an acoustic window is available so that an ultrasound system can create a focused ultrasound beam.

One example of an ultrasound technique for measuring mechanical properties of tissues, such as elasticity and viscosity, is called shear wave dispersion ultrasound vibrometry ("SDUV"). This SDUV technique is described, for example, in U.S. Pat. Nos. 7,753,847 and 7,785,259, which are herein incorporated by reference in their entirety. In SDUV, a focused ultrasound beam that operates within FDA regulatory limits, is applied to a subject to generate harmonic shear waves in a tissue of interest. The propagation speed of the induced shear wave is frequency dependent, or "dispersive," and relates to the mechanical properties of the tissue of interest. The motion of the tissue is measured using pulse-echo ultrasound techniques. Shear wave speeds at a number of frequencies are measured and subsequently fit with a theoretical dispersion model to inversely solve for tissue elasticity and viscosity. These shear wave speeds are estimated from the phase of tissue vibration that is detected between two or more points with known distance along the shear wave propagation path.

For a viscoelastic, homogenous, isotropic material, the shear wave speed, $c_s$, and shear wave attenuation, $\alpha_s$, are related to the complex shear modulus, $G^*(\omega)=G_s(\omega)+iG_l(\omega)$, by:

$$c_s(\omega) = \sqrt{\frac{2(G_s^2(\omega) + G_l^2(\omega))}{\rho\left(G_s(\omega) + \sqrt{G_s^2(\omega) + G_l^2(\omega)}\right)}} ; \quad (1)$$

$$\alpha_s(\omega) = \sqrt{\frac{\rho\omega^2\left(\sqrt{G_s^2(\omega) + G_l^2(\omega)} - G_s(\omega)\right)}{2(G_s^2(\omega) + G_l^2(\omega))}} ; \quad (2)$$

where $\rho$ is the density of the material; $\omega$ is the angular frequency of the shear wave; $G_s$, ($\omega$) is the storage or elastic modulus; and $G_l(\omega)$ is the loss or viscous modulus. Quantitative mechanical properties can be measured in a model independent manner if both shear wave speed and attenuation are known; however, measuring shear wave attenuation is challenging in the field of elasticity imaging. Typically, only shear wave speed is measured, and rheological models, such as Kelvin-Voigt, Maxwell, and Standard Linear Solid, are used to solve for complex shear modulus.

Acoustic radiation force has been used to study quasi-static viscoelastic properties of tissue. Transient characteristics of viscoelastic materials are known as creep and stress relaxation. Creep is a slow, progressive deformation of a material under constant stress. Stress relaxation is the gradual decrease of stress of a material under constant strain. Tissue creep response to an applied step-force by means of acoustic radiation force has been shown in several studies. In one such study, Mauldin, et al., reported a method for estimating tissue viscoelastic properties by monitoring the steady-state excitation and recovery of tissues using acoustic radiation force imaging and shear wave elasticity imaging. This method, called monitored steady-state excitation and recovery ("MSSER") imaging, described in U.S. Patent Application No. 2010/0138163, is an noninvasive radiation force-based method that estimates viscoelastic parameters by fitting rheological models, Kelvin-Voigt and Standard Liner Solid model, to the experimental creep strain response. However, as in shear wave propagation methods, a rheological model needs to be fit to the MSSER experimental data to solve for viscoelastic parameters.

Current elasticity imaging techniques are useful to indentify tissue mechanical properties; however, to quantify these properties a rheological model must be used, which introduces an undesirable amount of computational burden to the quantification process. In additional, rheological models may not describe the material behavior at all frequencies, may not be appropriate for the physical test being performed, and are less general than a model-free approach. It would therefore be desirable to provide a system and method for quantifying viscoelastic properties of tissue without the reliance on a model.

SUMMARY OF THE INVENTION

The present invention overcomes the aforementioned drawbacks by providing a system and method for model-independent quantification of tissue viscoelastic properties by estimating a complex shear modulus from a time-dependent creep response induced by acoustic radiation force. The creep response is generated and tissue viscoelastic parameters, such as complex shear modulus and loss tangent, are estimated using a formula that converts time-domain creep compliance to frequency domain complex modulus. Shear wave dispersion ultrasound vibrometry ("SDUV") is then used to calibrate the complex shear modulus so that knowledge of the applied radiation force magnitude is not necessary.

It is an aspect of the invention to provide a method for producing a viscoelastic tissue property metric using ultrasound. An acoustic force is applied to a tissue using an ultrasound system and a tissue displacement resulting from the applied acoustic force is measured. A relative complex shear modulus value is extracted from the measured tissue displacement, and a loss tangent is calculated from the extracted relative complex shear modulus. A viscoelastic tissue property metric is then calculated using the calculated loss tangent.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Viscoelastic materials exhibit transient characteristics such as creep and relaxation. Creep is a slow, progressive deformation of a material under constant stress. Stress relaxation is the gradual decrease of stress of a material under constant strain. In a shear creep test, the ratio between the unitless measured shear strain response, $\gamma(t)$, and the applied constant shear stress, $\tau_0$, is called the creep compliance, $J(t)$. By using the Boltzmann superposition principle, which states that the sum of the strain outputs resulting from each component of the stress input is the same as the strain output resulting from the combined stress input, the strain output under variable stress, $\tau(t)$, may be represented according to:

$$\gamma(t) = \int_0^t J(t-\xi)\frac{\partial \tau(\xi)}{\partial \xi} d\xi; \qquad (3)$$

where $\gamma$ is the shear strain, $\tau$ is the shear stress, J is creep compliance, and $\xi$ is an independent variable. Eqn. (3) is known as the integral representation of viscoelastic constitutive equations, and illustrates how the complex shear modulus, $G^*(\omega)$, is related to the time-domain creep compliance, $J(t)$, by a convolution operation. This relationship becomes much clearer when modifying Eqn. (3) using the Fourier transform convolution and derivative properties, such that the complex shear modulus may be written as:

$$G^*(\omega) = \frac{FT\{\tau(t)\}}{FT\{\gamma(t)\}} = \frac{1}{i\omega FT\{J(t)\}}; \qquad (4)$$

where $F\{\ldots\}$ is the Fourier transform operation. Because creep compliance, $J(t)$, is a function that grows with increasing time, its Fourier transform is not a convergent integral. Recently, an analytic solution of Eqn. (4) was reported by R. M. L. Evans, et al., in "Direct Conversion of Rheological Compliance Measurements into Storage and Loss Moduli," *Phys. Rev. E*, 2009; 80: 012501. This analytical solution takes advantage of the properties of the Fourier transform. Briefly, the second derivative of the creep compliance vanishes with time; therefore, its Fourier transform exists. The time-creep compliance to complex modulus conversion described by Evans, et al., is:

$$G^*(\omega) = \frac{i\omega}{i\omega J(0) + (1-e^{-i\omega t(1)})\frac{J(1)-J(0)}{t(1)} + \frac{e^{-i\omega t(N)}}{\eta} + \ldots + \sum_{n=2}^{N}\left(\frac{J(n)-J(n-1)}{t(n)-t(n-1)}\right)(e^{-i\omega t(n-1)} - e^{-i\omega t(n)})}; \qquad (5)$$

where $t(0)=0$; and $J(0)$ and $\eta$ are the compliance at $n=0$ and the steady-state viscosity, respectively. The value of $J(0)$ is estimated by extrapolation of the compliance function as $t \to 0$. Similarly, the steady-state viscosity, $\eta$, is estimated by extrapolation of the compliance function as $t \to \infty$. The frequency range of $G^*(\omega)$ depends on the temporal resolution (the time of the first data point, $t(1)$) and duration (the time of the last data point, $t(N)$) of the acquired data set. The advantage of using Eqn. (5) to convert the time-dependent compliance, $J(t)$, to complex shear modulus, $G^*(\omega)$, is that no fitting of data to a theoretical model is required. Thus, the desired tissue mechanical properties can be recovered for a range of frequencies without the use of a model.

Acoustic radiation force can be used to apply a step-stress input, $\tau_0$, that causes creep in a viscoelastic material. The displacement, $u(t)$, and creep compliance, $J(t)$, relation may then be described as follows:

$$J(t) = \frac{\gamma(t)}{\tau_0} = \frac{u(t)/L}{F_0/A}; \quad (6)$$

where $\gamma(t)$ is the unitless measured creep strain defined as measured displacement $u(t)$ per unit length L, assuming that geometry and boundary conditions do not change with time; and $\tau_0$ is the applied stress defined as applied force, $F_0$ per unit area, A. However, the actual applied force, $F_0$, is generally unknown; as a consequence, the magnitude of the applied stress, $\tau_0$, is also unknown. In addition, ultrasound motion detection applications usually estimate displacement responses instead of strain response. Assuming that the material is linear, the creep compliance, $J(t)$, is linearly proportional to displacement, $u(t)$, according to:

$$J(t) = \beta \cdot u(t) \quad (7);$$

where $\beta$ is a proportionality constant that relates the magnitude of the step-stress, $\sigma_0$, and the length, L, of an infinitesimal cube. By combining Eqns. (4) and (7), the complex shear modulus, $G^*(\omega)$, can be extracted from the displacement, $u(t)$, relative to the constant, $\beta$, according to:

$$G^*(\omega) = \frac{1}{i\omega\beta \cdot FT\{u(t)\}}. \quad (8)$$

Calling the extracted relative complex modulus, $C^*(\omega)$, it can be written in a form where it is relative to the complex shear modulus, $G^*(\omega)$, by the constant, $\beta$, $$C^*(\omega) = \beta(G_s(\omega) + iG_l(\omega)) \quad (9);$$

where $G_s(\omega)$ and $G_l(\omega)$ are the real and imaginary parts of the complex shear modulus, $G^*(\omega)$, respectively. The real part, $G_s(\omega)$, is associated with energy storage and release during periodic deformation; thus, it is referred to as the elastic or storage modulus. The imaginary part, $G_l(\omega)$, is associated with the dissipation of energy that is transformed into heat; thus, it is referred to as the viscous or loss modulus.

Because the magnitude of the acoustic radiation force, $F = 2\alpha I/c$ is proportional to the absorption coefficient of the media, $\alpha$, and the temporal average intensity of the acoustic beam at a given spatial location, I, in a homogenous material, the magnitude of the extracted relative complex modulus, $C^*(\omega)$, will vary as a function of material absorption and acoustic beam intensity. Thus, the extracted relative complex modulus, $C^*(\omega)$, is not, in and of itself, a useful measure. To overcome this problem, a property of viscoelastic materials called loss tangent, or $\tan(\delta)$, is used. Loss tangent is defined as the ratio between the loss modulus and the storage modulus:

$$\tan(\delta) = \frac{C_l(\omega)}{C_s(\omega)} = \frac{\beta G_l(\omega)}{\beta G_s(\omega)} = \frac{G_l(\omega)}{G_s(\omega)}; \quad (10)$$

where $C_s(\omega)$ and $C_l(\omega)$ are the real and imaginary parts of the extracted relative complex modulus, $C^*(\omega)$, respectively. The loss tangent is associated with the damping capacity of a viscoelastic material. To solve for the actual complex shear modulus over a range of frequencies, the function described in Eqn. (9) can be calibrated as described below.

The wavenumber, k, and the shear elastic modulus, G, are related through the shear wave propagation equation. In an elastic medium, they are related by:

$$G = \rho \frac{\omega^2}{k^2}; \quad (11)$$

where $\rho$ is the density of the medium and $\omega$ is the angular frequency. In the case of a linear viscoelastic medium, the wavenumber, k, and shear elastic modulus, G, are complex values, and may be written as:

$$k^* = k_r - ik_i \quad (12);$$

and $$G^* = G_s + iG_l. \quad (13);$$

where $k_r$ and $k_i$ are the real and imaginary parts of the wavenumber, respectively; and $G_s$ and $G_l$ are the real and imaginary parts of the shear elastic modulus. As noted above, $G_s$ is the storage shear modulus or shear elastic modulus, and $G_l$ is the loss shear modulus or shear viscous modulus. The real and imaginary parts of the wavenumber are defined as follows:

$$k_r = \frac{\omega}{c_s}; \quad (14)$$

$$k_i = \alpha_s; \quad (15)$$

where $c_s$ is the shear wave speed and $\alpha_s$ is the shear wave attenuation. For a viscoelastic medium, Eqn. (11) can be rewritten as:

$$G_s(\omega) = \rho\omega^2 \left( \frac{k_r^2 - k_i^2}{k_r^2 + k_i^2} \right); \quad (16)$$

$$G_l(\omega) = -2\rho\omega^2 \frac{k_r k_i}{k_r^2 + k_i^2}. \quad (17)$$

The loss tangent may be written in terms of the complex wavenumber, $k^*$, as:

$$\tan(\delta) = \frac{2k_r k_i}{k_r^2 - k_i^2}. \quad (18)$$

If both $\tan(\delta)$ and $k_r$ are known, the negative root for $k_i$ in Eqn. (18) may be given as:

$$k_i = k_r \left( \left( \frac{1}{\tan(\delta)} \right) - \sqrt{\left( 1 - \left( \frac{1}{\tan(\delta)} \right)^2 \right)} \right). \quad (19)$$

By knowing $k_r$ and $k_i$, the shear storage and loss moduli may be obtained from Eqns. (16) and (17).

Figure 1:
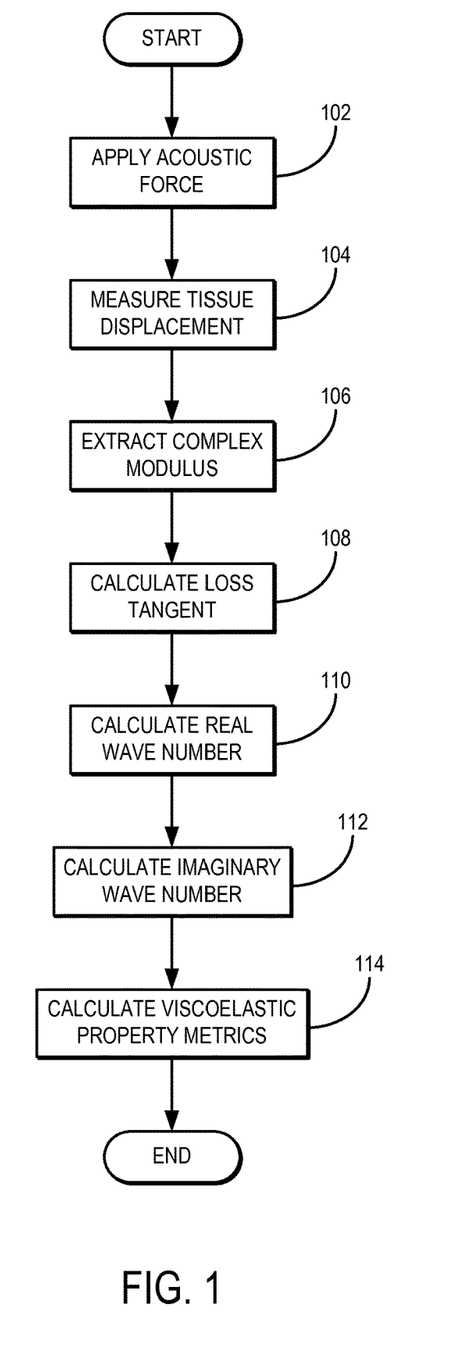
FIG. 1 is a flowchart setting forth the steps of an example of a method for calculating viscoelastic properties of a tissue using ultrasound and without the need of a tissue model.
Figure 2A:
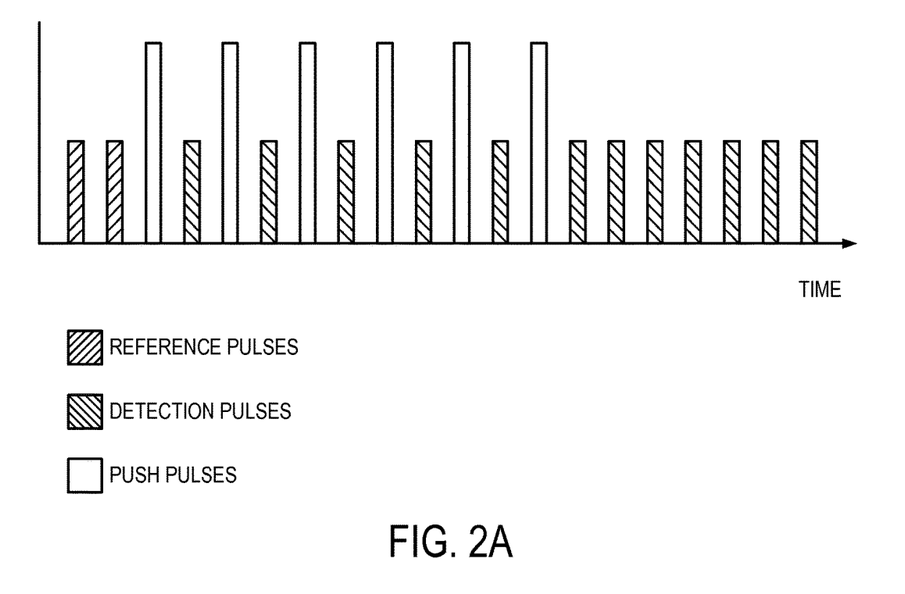
FIG. 2A is a pictorial representation of an example of an ultrasound beam sequence that may be used for applying an acoustic force to a tissue and measuring displacement therefrom, the beam sequence including both push and detect beams.

Referring now to FIG. 1, a flowchart setting forth the steps of a method for calculating viscoelastic properties of a tissue using ultrasound and without the need of a tissue model is illustrated. The method begins with the application of an applied mechanical stress, such as an acoustic force, to the tissue, as indicated at step 102. As an example of how the acoustic force may be generated, high intensity pushing beams are interspersed with conventional intensity tracking beams during a creep period. The push-tracking beams mimic a temporal step-force while creep displacements are tracked through the creep period, as discussed below. Additionally, two reference tracking beams may be used before the creep period and additional tracking beams may follow cessation of the acoustic force. An example of such a beam sequence is illustrated in FIG. 2A.

Figure 2B:
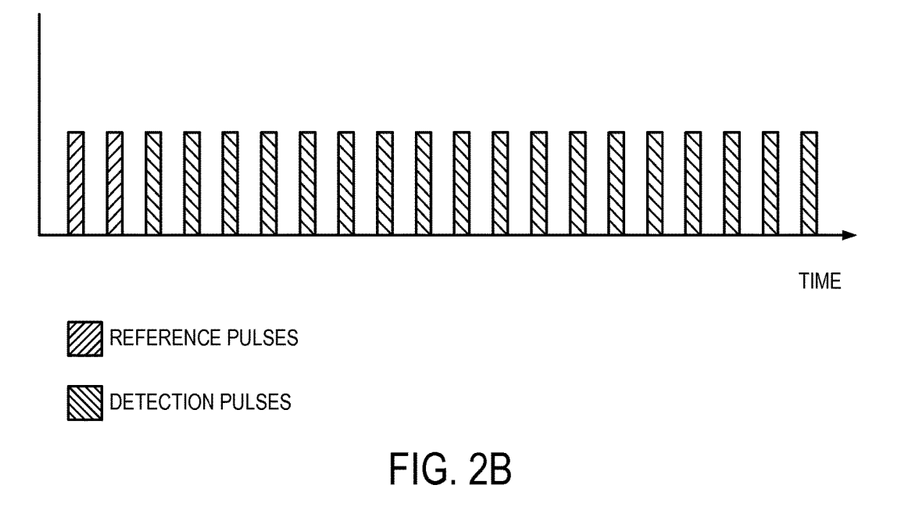
FIG. 2B is a pictorial representation of an example of an ultrasound beam sequence that may be used for applying an acoustic force to a tissue and measuring displacement therefrom, the beam sequence including only detect beams.

Conventional detect beams can also be used to generate and detect tissue transient motion simultaneously. An example of such a beam sequence is illustrated in FIG. 2B. Compared to the beam sequence in FIG. 2A, tissue motion can be tracked at a higher pulse repetition frequency ("PRF") with the beam sequence in FIG. 2B, thereby allowing measurements of complex modulus at higher frequencies. The tissue motion produced by the beam sequence in FIG. 2B may be lower than that produced by the beam sequence in FIG. 2A, which can lower the signal-to-noise ratio ("SNR") and reliability of measurements when using the beam sequence in FIG. 2B. To increase tissue motion when using the beam sequence in FIG. 2B, higher transmit voltages can be used for the detection pulses. In addition, the PRF can also be increased to produce more tissue motion. The detection pulses in FIG. 2B can be spaced closer together in time compared to the pulses in the beam sequence illustrated in FIG. 2A because there are no push pulses interlaced between adjacent detection pulses. Finally, in the beam sequence of FIG. 2B, the duration of each detection pulse can be lengthened to increase tissue motion. In pulse-echo ultrasound detection, the transmitted detection pulse is usually very short (about one ultrasound cycle) to maintain good axial resolution. In the beam sequence illustrated in FIG. 2B, longer detection pulses (up to 10 cycles or more) can be used because tissue motion should be relatively uniform along axial depth in the focal region. As a result, lower axial resolution associated with the longer detection pulses can be tolerated. A benefit of using longer detection pulses is higher SNR in pulse-echo and, thus, higher SNR in motion detection. The result is that motion due to detection pulses alone should be sufficient for the ultrasound creep measurements described herein.

The displacement in the tissue resulting from this applied acoustic force is then measured, as indicated at step 104. A relative complex modulus is extracted from the measured displacement, as indicated at step 106. For example, Eqn. (8)#8 is used to extract the relative complex modulus from the tissue displacement measurement. Using the extracted relative complex modulus, a loss tangent is calculated, as indicated at step 108. By way of example, Eqn. (10) is used to calculate the loss tangent. Viscoelastic properties of the tissue are then calculated using this loss tangent. The real component of a wavenumber is calculated to help in this process, as indicated at step 110. The real component of the wavenumber may be calculated in accordance with Eqn. (14) using known or measured information about the angular frequency and wave speed of the shear waves induced by the applied acoustic force. Using the real component of the wavenumber and the calculated loss tangent, the imaginary component of the wavenumber is calculated, as indicated at step 112. For example, Eqn. (19) may be used to calculate the imaginary component of the wavenumber. Together, the real and imaginary components of the wavenumber are then used to calculate viscoelastic properties of the tissue, such as shear elastic modulus and shear viscous modulus, as indicated at step 114. These metrics may be calculated using, for example, Eqns. (16) and (17), respectively.

When the magnitude of the radiation force is increased by a factor of n, a proportional increase in displacement is expected for linear viscoelastic materials. Moreover, the extracted relative complex modulus is also expected to be proportional to the acoustic radiation force magnitude, but the estimated loss tangent is expected to be independent of force magnitude and geometry. Because there may be instances where loss tangent is the same for materials with different storage and loss moduli, SDUV may be used in combination with acoustic radiation force creep to estimate the true complex modulus. For example, SDUV may be used to estimate shear wave speed over a range of frequencies, then both loss tangent and shear wave speeds may be used to estimated shear wave attenuation values, which may then be used to estimate model-free complex moduli.

Systems and methods for fully quantifying viscoelastic parameters in a manner independent of rheological or other models using by acoustic radiation force creep and shear wave dispersion ultrasound vibrometry ("SDUV") have been provided. Previous work in this area involved the use of rheological models, but the need for such models affects the viscoelastic parameter estimation and fitting processes. The described acoustic radiation force creep method uses a conversion formula that is the analytic solution of a constitutive equation. This conversion formula is shown to be sensitive to sampling frequency, the first reliable measure in time, and the long term viscosity approximation.

Acoustic radiation force creep in combination with a creep-compliance to complex modulus conversion formula provides a non-invasive, fast, robust, and local measure of tissue viscoelasticity. Clinical applications of this novel method are highly supported because it only requires pushing beams similar to the acoustic radiation force imaging ("ARFI") method, which is currently implemented on commercial ultrasound scanning machines. Moreover, the alternative ultrasound beam sequence illustrated in FIG. 2B, where only detect beams are used for both creep production and detection, is highly compatible with conventional ultrasound systems. Thus, tissue heating using the provided method is expected to be below FDA limits.

Figure 3:
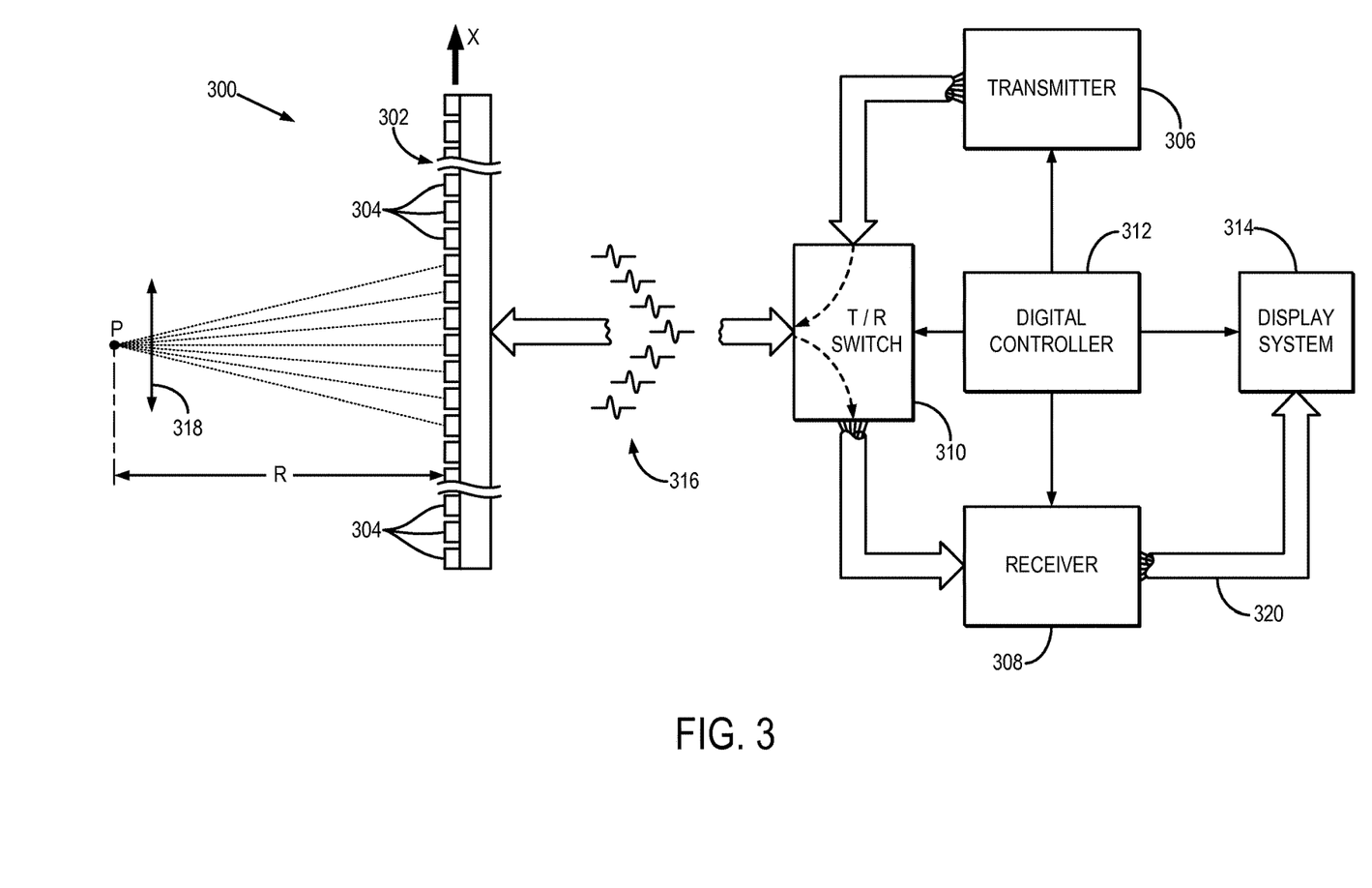
FIG. 3 is a block diagram of an example ultrasound system that includes a linear array ultrasound transducer.

Referring now to FIG. 3, an example of an ultrasound imaging system 300 that may be used for implementing the present invention is illustrated. It will be appreciated, however, that other suitable ultrasound systems can also be used to implement the present invention. The ultrasound imaging system 300 includes a transducer array 302 that includes a plurality of separately driven transducer elements 304. When energized by a transmitter 306, each transducer element 302 produces a burst of ultrasonic energy. The ultrasonic energy reflected back to the transducer array 302 from the object or subject under study is converted to an electrical signal by each transducer element 304 and applied separately to a receiver 308 through a set of switches 310. The transmitter 306, receiver 308, and switches 310 are operated under the control of a digital controller 312 responsive to the commands input by a human operator. A complete scan is performed by acquiring a series of echo signals in which the switches 310 are set to their transmit position, thereby directing the transmitter 306 to be turned on momentarily to energize each transducer element 304. The switches 310 are then set to their receive position and the subsequent echo signals produced by each transducer element 304 are measured and applied to the receiver 308. The separate echo signals from each transducer element 304 are combined in the receiver 308 to produce a single echo signal that is employed to produce a line in an image, for example, on a display system 314.

The transmitter 306 drives the transducer array 302 such that an ultrasonic beam is produced, and which is directed substantially perpendicular to the front surface of the transducer array 302. To focus this ultrasonic beam at a range, R, from the transducer array 302, a subgroup of the transducer elements 304 are energized to produce the ultrasonic beam and the pulsing of the inner transducer elements 304 in this subgroup are delayed relative to the outer transducer elements 304, as shown at 316. An ultrasonic beam focused at a point, P, results from the interference of the separate wavelets produced by the subgroup of transducer elements 304. The time delays determine the depth of focus, or range, R, which is typically changed during a scan when a two-dimensional image is to be performed. The same time delay pattern is used when receiving the echo signals, resulting in dynamic focusing of the echo signals received by the subgroup of transducer elements 304. In this manner, a single scan line in the image is formed.

To generate the next scan line, the subgroup of transducer elements 304 to be energized are shifted one transducer element 304 position along the length of the transducer array 302 and another scan line is acquired. As indicated at 318, the focal point, P, of the ultrasonic beam is thereby shifted along the length of the transducer 302 by repeatedly shifting the location of the energized subgroup of transducer elements 304.

Figure 4:
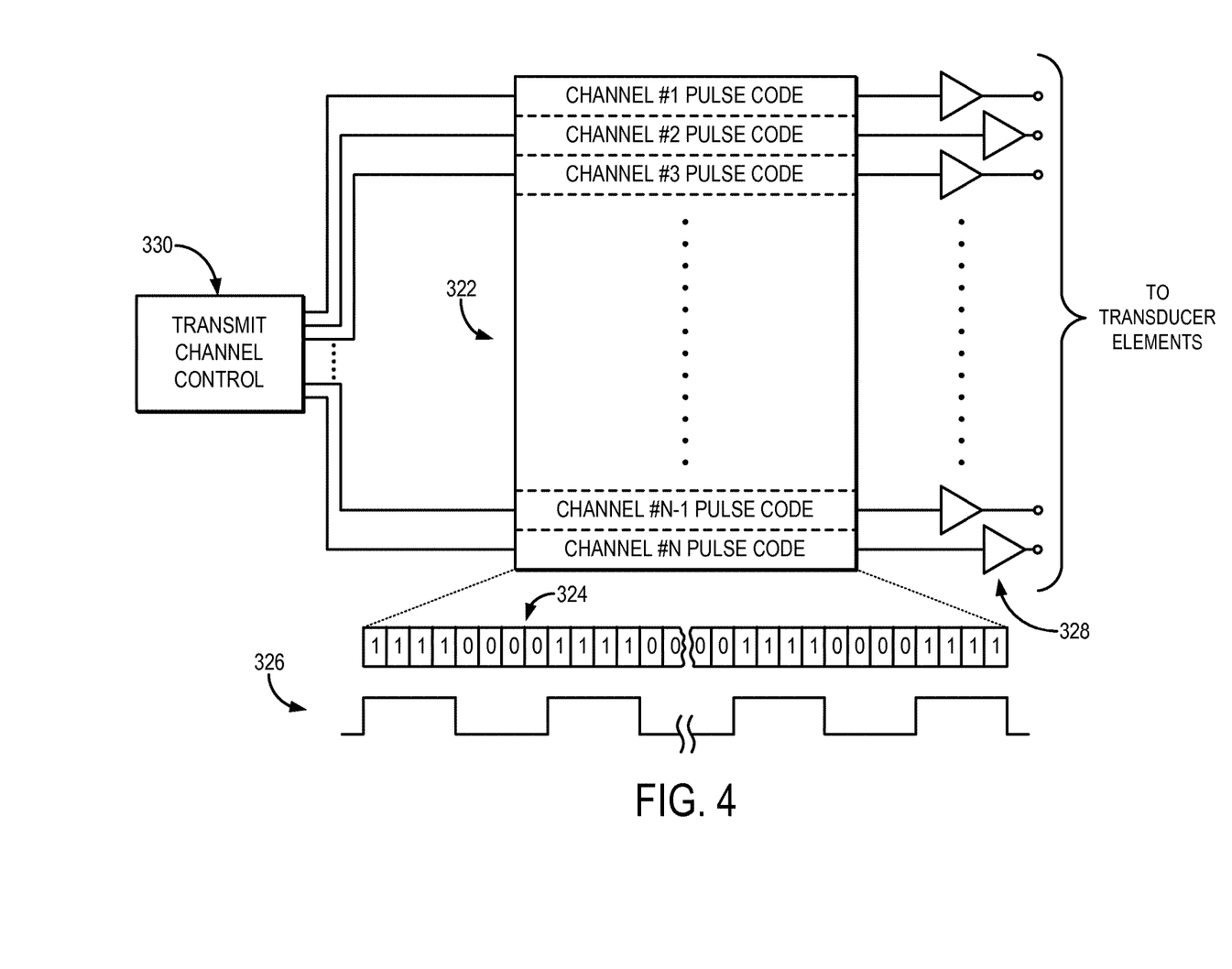
FIG. 4 is a block diagram of an example of a transmitter that forms a part of the ultrasound system of FIG. 3.

Referring particularly to FIG. 4, the transmitter 306 includes a set of channel pulse code memories, which are indicated collectively at 322. In general, the number of pulse code memories 322 is equal to the number of transducer elements 304 in the transducer 302. These pulse code memories are also referred to as transmission channels for this reason. Each pulse code memory 322 is typically a 1×N bit memory that stores a bit pattern 324 that determines the frequency of the ultrasonic pulse 326 that is to be produced. This bit pattern 324 may be read out of each pulse code memory 322 by a master clock and applied to a driver 328 that amplifies the signal to a power level suitable for driving the transducer 302. In the example shown in FIG. 4, the bit pattern is a sequence of four "1" bits alternated with four "0" bits to produce a five megahertz ultrasonic pulse 326. The transducer elements 304 to which these ultrasonic pulses 326 are applied respond by producing ultrasonic energy. If all of the available bits are used, a pulse with a narrow bandwidth centered on the carrier frequency will be emitted.

Figure 5:
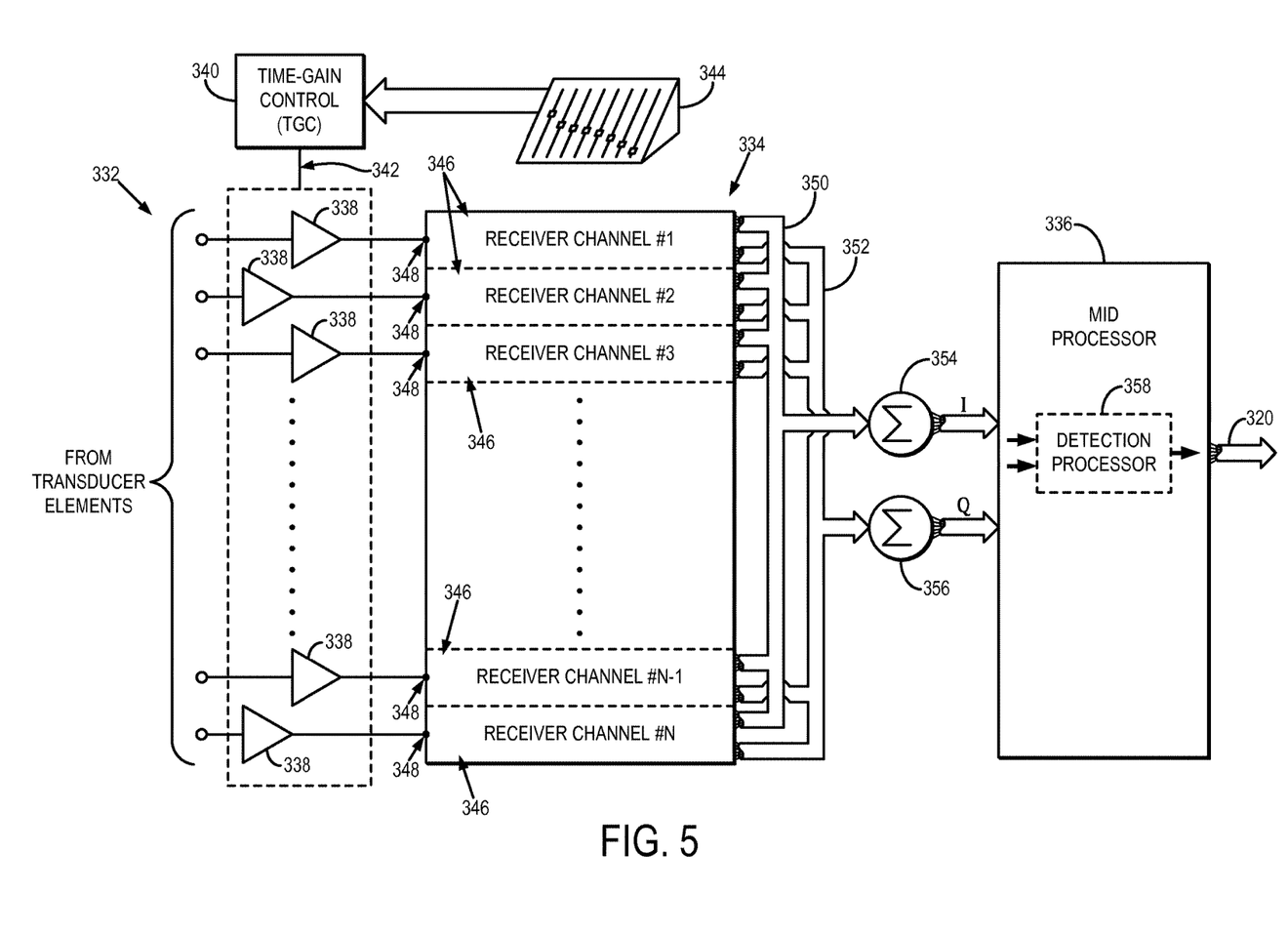
FIG. 5 is a block diagram of an example of a receiver that forms a part of the ultrasound system of FIG. 3.

Referring particularly to FIG. 5, the receiver 308 is comprised of three sections: a time-gain control section 332, a beam forming section 334, and a mid-processor section 336. The time-gain control section 332 includes an amplifier 338 for each receiver channel in the receiver 308, and a time-gain control circuit 340. The input of each amplifier 338 is connected to a respective one of the transducer elements 304 to receive and amplify the echo signal that is receives from the respective transducer element 304. The amount of amplification provided by the amplifiers 338 is controlled through a control line 342 that is driven by the time-gain control circuit 340. As the depth, or range, R, of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by a user who manually sets time-gain control potentiometers 344 to values that provide a relatively uniform brightness over the entire range of the sector scan. The time interval over which the echo signal is acquired determines the range from which it emanates, and this time interval is divided into, for example, eight segments by the time-gain control circuit 340. The settings of the time-gain control potentiometers 344 are employed to set the gain of the amplifiers 338 during each of the respective time intervals so that the received echo signal is amplified in ever increasing amounts over the acquisition time interval.

The beam forming section 334 of the receiver 308 includes a plurality of separate receiver channels 346. As will be explained in more detail below, each receiver channel 346 receives an analog echo signal from one of the amplifiers 338 at an input 348, and produces a stream of digitized output values on an in-phase, I, bus 350 and a quadrature, Q, bus 352. Each of these I and Q values represents a sample of the echo signal envelope at a specific range, R. These samples have been delayed in the manner described above such that when they are summed with the I and Q samples from each of the other receiver channels 346 at summing points 354 and 356, they indicate the magnitude and phase of the echo signal reflected from a point, P, located at range, R, on the steered beam, θ.

The mid-processor section 336 receives beam samples from the summing points 354 and 356. The I and Q values of each beam sample may be, for example, a 16-bit digital number that represents the in-phase, I, and quadrature, Q, components of the magnitude of the echo signal from a point (R,θ). The mid-processor 336 can perform a variety of calculations on these beam samples, the choice of which is determined by the type of imaging application at task.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a viscoelastic tissue property metric using ultrasound, the steps of the method comprising:
   a) applying a mechanical stress to a tissue using an ultrasound system;
   b) measuring over a time period, a tissue displacement, u(t), resulting from the applied mechanical stress using the ultrasound system;
   c) calculating with the computer system, a loss tangent from real and imaginary parts of relative complex modulus values computed from the tissue displacement, u(t), measured over the time period; and
   d) calculating with the computer system, at least one viscoelastic tissue property metric using the calculated loss tangent.

2. The method as recited in claim 1 in which step d further includes calculating a real part of a wavenumber using a frequency and wave speed of shear waves generated in the tissue by the applied mechanical stress, and using the real part of the wavenumber to calculate the at least one viscoelastic tissue property metric.

3. The method as recited in claim 1 in which step d includes calculating an imaginary part of a wavenumber using the loss tangent and using the imaginary part of the wavenumber to calculate the at least one viscoelastic tissue property metric.

4. The method as recited in claim 1 in which step d includes:
   i) calculating a real part of a wavenumber using a frequency and wave speed of shear waves generated in the tissue by the applied mechanical stress;
   ii) calculating an imaginary part of a wavenumber using the loss tangent and the calculated real part of the wavenumber; and iii) calculating the at least one viscoelastic tissue property metric using the calculated real and imaginary parts of the wavenumber.

5. The method as recited in claim 1 in which the at least one viscoelastic tissue property metric is at least one of a storage modulus and a loss modulus.

6. The method as recited in claim 1 in which the tissue displacement is measured using ultrasound energy to detect the tissue displacement.

7. The method as recited in claim 6 in which the mechanical stress applied in step a) is generated by the ultrasound energy used to detect the tissue displacement in step b).

8. An ultrasound system for measuring a viscoelastic property of a tissue, comprising:
   an ultrasound transducer configured to transmit ultrasound energy and to receive acoustic signals responsive to the transmitted ultrasound energy;
   a processor in communication with the ultrasound transducer, the processor being configured to:
   direct the ultrasound transducer to apply an acoustic force to a tissue;
   receive signals responsive to the acoustic force from the tissue;
   measure over a period of time, tissue displacement, u(t), from the received signals;
   calculate a loss tangent from real and imaginary parts of relative complex modulus values computed from the tissue displacement, u(t), measured over the period of time; and
   calculate at least one viscoelastic tissue property metric using the calculated loss tangent.

9. The ultrasound system as recited in claim 8 in which the processor is configured to calculate a real part of a wavenumber using a frequency and wave speed of shear waves generated in the tissue by the applied acoustic force, and to use the real part of the wavenumber to calculate the at least one viscoelastic tissue property metric.

10. The ultrasound system as recited in claim 8 in which the processor is configured to calculate an imaginary part of a wavenumber using the calculated loss tangent and to use the imaginary part of the wavenumber to calculate the at least one viscoelastic tissue property metric.

11. The ultrasound system as recited in claim 8 in which the processor is configured to:
    calculate a real part of a wavenumber using a frequency and wave speed of shear waves generated in the tissue by the applied acoustic force;
    calculate an imaginary part of a wavenumber using the calculated loss tangent and the calculated real part of the wavenumber; and
    calculate the at least one viscoelastic tissue property metric using the calculated real and imaginary parts of the wavenumber.

12. The ultrasound system as recited in claim 8 in which the processor is configured to calculate the at least one viscoelastic tissue property metric as at least one of a storage modulus and a loss modulus.

\* \* \* \* \*